United States Patent [19]

Flournoy

[11] 4,075,601
[45] Feb. 21, 1978

[54] COMBINED PIPELINE MARKER AND TEST UNIT

[75] Inventor: Norman E. Flournoy, Richmond, Va.

[73] Assignee: Texaco Inc., New York, N.Y.

[21] Appl. No.: 588,928

[22] Filed: June 20, 1975

[51] Int. Cl.$^2$ ............................................. H04B 11/00
[52] U.S. Cl. ................................... 340/15; 73/40.5 A
[58] Field of Search ................. 340/1 R, 15, 236, 239, 340/242; 73/40.5 A, 40.5 R, 67.7; 324/34 R, 67

[56] References Cited

U.S. PATENT DOCUMENTS

| | | | |
|---|---|---|---|
| 2,820,959 | 1/1958 | Bell | 324/67 |
| 2,940,302 | 6/1960 | Scherbatskoy | 73/40.5 A |
| 3,102,252 | 8/1963 | Bolton | 340/15 |
| 3,561,256 | 2/1971 | Bustin et al. | 73/40.5 A |
| 3,685,008 | 8/1972 | Bhuta et al. | 73/67.7 |
| 3,800,270 | 3/1974 | Bailey | 340/1 R |
| 3,859,846 | 1/1975 | Asada et al. | 73/67.7 |

OTHER PUBLICATIONS

Dean et al., RCA Publication: Digital Integrated Circuits, Mar. 1971, Application Note ICAN 6267.
*Guidebook of Electronic CKTS.*, J. Markus, McGraw-Hill, Inc., pp. 600, 995.

*Primary Examiner*—Maynard R. Wilbur
*Assistant Examiner*—T. M. Blum
*Attorney, Agent, or Firm*—Thomas H. Whaley; Carl G. Ries; Henry C. Dearborn

[57] ABSTRACT

An acoustic type of pipeline marker that has combined with it, as a unitary structure, an acoustic signal detector for determining whether the marker is operating. The detector is only energized when it is desired to check whether the marker is emitting the desired acoustic signals into the pipeline. The detector provides a visual signal.

1 Claim, 4 Drawing Figures

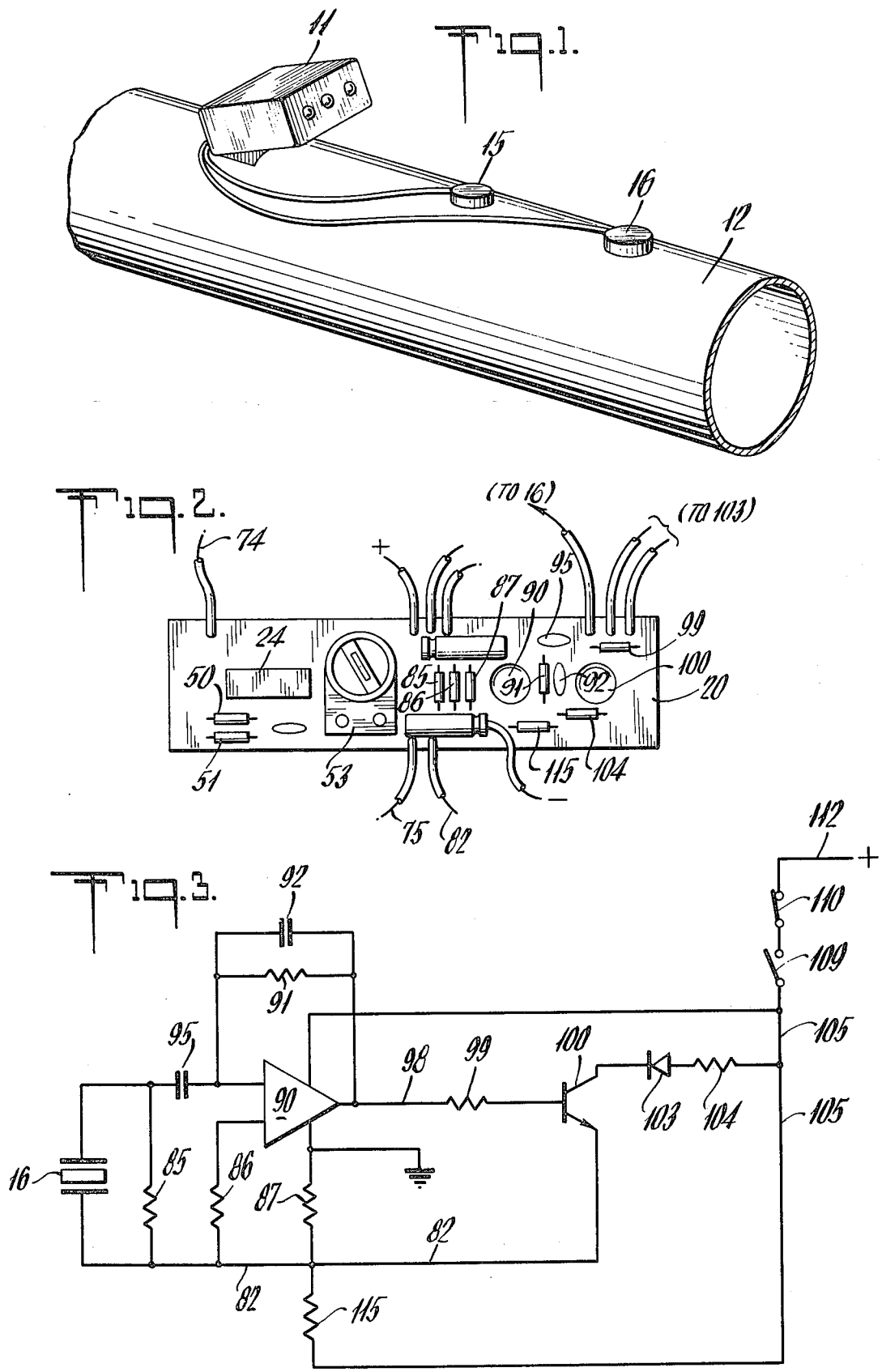

COMBINED PIPELINE MARKER AND TEST UNIT

BACKGROUND OF THE INVENTION

1. Field of the Invention

This invention relates to acoustic type pipeline surveying, in general. More specifically, it concerns a unitary marker structure with a self-testing element in conjunction therewith.

2. Description of the Prior Art

The concept of applying markers of one sort or another to a pipeline at predetermined intervals, in order to note passage of surveying pigs or the like, is quite well known. However, in order for such a pipeline marker signal generator to be effective, it is important that the fact of continuing operation is known.

Consequently, it is an object of this invention to provide the combination of a simplified acoustic pipeline marker which includes a detector that can be momentarily energized and will pick-up the marker signal if it exists, with provision for a visual indicator.

SUMMARY OF THE INVENTION

Briefly, the invention concerns a combined pipeline marker and self test unit which comprises in combination a first piezoelectric crystal adapted for bonding to said pipeline for emitting an acoustic marker signal, and a low power oscillator for driving said crystal. It also comprises a second piezoelectric crystal adapted for bonding to said pipeline adjacent to said first piezoelectric crystal, and a low power amplifier for amplifying signals generated by said second crystal. It also comprises an indicator means connected to the output of said amplifier for verifying the output of said marker signal.

Once more briefly, the invention concerns a combined pipeline marker and self test unit which comprises in combination a first piezoelectric crystal adapted for bonding to said pipeline for emitting an acoustic marker signal, and a low power oscillator that comprises a CMOS integrated circuit having six inverting buffers. The oscillator also comprises circuit means including a capacitor and two resistors connected to a pair of said buffers for producing a predetermined frequency oscillation. Three of said buffers are connected in parallel to drive said first crystal. One of the said buffers is connected between said oscillation pair and said three drive buffers to isolate said oscillation pair. The test unit also comprises a second piezoelectric crystal adapted for bonding to said pipeline adjacent to said first piezoelectric crystal for detecting the presence of said marker signal, and a low power amplifier for amplifying signals generated by said second crystal. The said low power amplifier comprises an integrated circuit amplifier, and a discrete transistor connected to the output of said integrated amplifier. It also comprises filter means for connecting said second crystal to said integrated amplifier for tuning it to said predetermined oscillation frequency. The unit also comprises a light emitting diode connected to the output of said transistor for indicating presence of said marker signal, and switch means for energizing said low power amplifier to test said marker operation.

BRIEF DESCRIPTION OF THE DRAWINGS

The foregoing and other objects and benefits of the invention will be more fully set forth below in connection with the best mode contemplated by the inventor of carrying out the invention, and in connection with which there are illustrations provided in the drawings, wherein:

FIG. 1 is a perspective showing a portion of a pipeline with unit according to the invention mounted thereon;

FIG. 2 is a plan view illustrating the circuit board lay-out that is employed with a unit according to FIG. 1;

FIG. 3 is a circuit diagram illustrating the detector circuit of the test element portion of the unit.

DESCRIPTION OF THE PREFERRED EMBODIMENT

Figure 4:
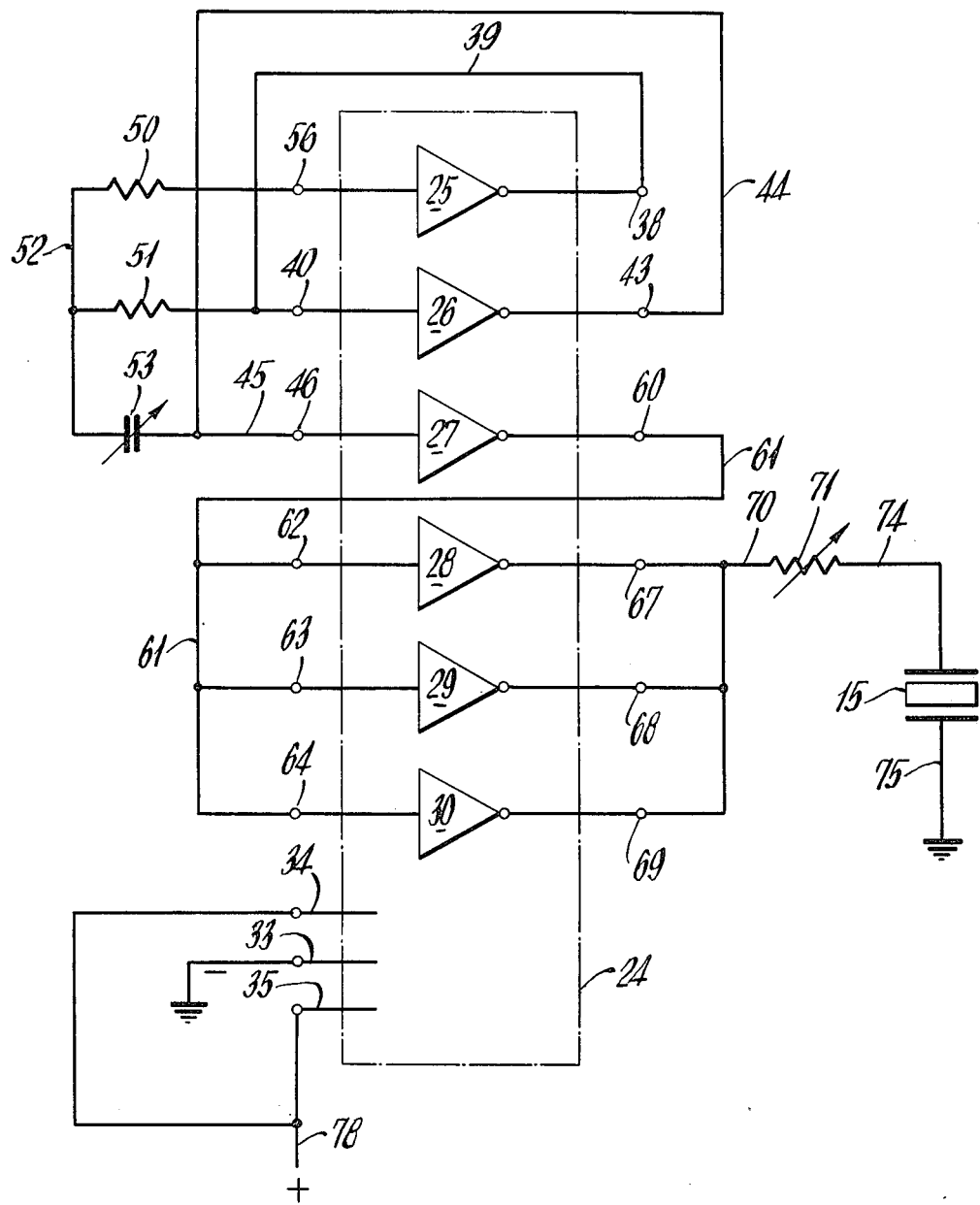
FIG. 4 is a circuit diagram of the oscillator and driver elements employed in the marker portion of the pipeline unit.

When investigating pipelines with pig type instruments for determining leaks or other acoustic related conditions, it is often desirable to mark pipeline locations on the data being recorded by the pig. Piezoelectric and magnetic signal generators have been used to produce ultrasonic vibrations which travel through the pipe wall and into the fluid media where they are detected by a sensor on the pig. In the case of the ultrasonic leak detector, the same sensor can be used to detect both leak sounds and the sounds of a marker generator. This invention provides for a highly simple yet extremely effective generating marker for producing the desired ultrasonic vibration at a predetermined frequency.

The invention also relates to a combination unitary instrument that includes in addition to a simple ultrasonic generator of marker signals, a receiver or test unit for periodically checking to determine whether the generator is properly producing the ultrasonic signals desired.

FIG. 1 illustrates an embodiment of a combined marker and self-test unit which includes a housing 11 that may be supported or conveniently mounted on or adjacent to a pipeline 12. The unit includes a first piezoelectric crystal 15 and second piezoelectric crystal 16. These crystals are physically mounted in housings for protecting against weathering conditions, and are adapted for mounting firmly with good acoustic coupling to the outside surface of the pipeline 12.

As will appear more fully hereafter, one of the crystals 15 or 16 is connected electrically into a circuit that makes up the generator, or marker signal circuit of the unit. The other is connected as a receiver crystal which has its electrical circuit connection leading to an amplifier and circuit arrangement for indicating the presence of ultrasonic vibrations in the pipeline.

FIG. 2 illustrates a circuit board 20 which has most of the electrical elements of the unit mounted thereon, and which is mounted inside of the housing 11. In addition, the housing 11 has interior space for including the necessary batteries (not shown) which, in the particular embodiment illustrated, may be eight D-sized dry cells.

FIG. 4 is a circuit diagram of the generator. It will be noted that it is a low cost, low power, very simple system. A major element is a CMOS integrated circuit 24 that is shown enclosed in dashed lines and that includes six inverting buffers 25–30. In addition there is a ground circuit terminal 33 and two high voltage terminals or electrodes 34 and 35. It should be noted that it is now well understood in the electronic industry that the abbreviation CMOS stands for Complimentary Metal Oxide Semiconductor.

The CMOS integrated circuit 24 has the buffers 25 and 26 connected to form an oscillator by having a terminal 38 connected via a circuit connection 39 to another terminal 40 which goes to the input side of the buffer 26. A terminal 43 is connected to the output side of the buffer 26, and it has a circuit connection 44 connected thereto which joins another circuit connection 45 that goes to a terminal 46. The terminal 46 goes to the input of the buffer 27 which, as will be explained further below, acts as an isolating buffer between the oscillator and the output drive for the oscillator system.

The oscillator portion of the circuit is made up of the buffers 25 and 26 with circuit connections already mentioned, and it includes a resistor 50 as well as another resistor 51 that are both connected to a common circuit connection 52. The circuit connection 52 also goes to one side of a variable capacitor 53.

It may be noted that one end of the resistor 50 is connected to a terminal 56 of the CMOS 24. This terminal is an input connection for the buffer 25. It will be understood that the particular values for resistors 50, 51, and capacitor 53 will basically determine the oscillation frequency although it will vary slightly with variations in supply voltage.

The output of the oscillator is connected from the terminal 46 into the isolating buffer 27, and then it goes via a terminal 60 that has a circuit connection 61 which leads from the terminal 60 to all three terminals 62, 63 and 64, in parallel. These three terminals 62–64 are connected to the inputs of the buffers 28, 29 and 30, while the outputs from these buffers go via terminals 67, 68 and 69 (in parallel) to a circuit connection 70 which goes to one end of an optional variable resistor 71. The other end of the resistor 71 goes via a circuit connection 74 to one electrode of the crystal 15 which has its other electrode connected to a ground circuit via a circuit connection 75. It will be noted that there is an input circuit connection 78 for the oscillator system. It is designed to have a positive voltage source, such as a battery or batteries, connected for supplying a DC positive potential.

Referring to FIG. 3, there is shown a circuit diagram for the low power amplifier of the combined system. This acts to amplify and indicate the presence of acoustic signals. Such signals are picked up by the crystal 16 that is bonded to the pipeline 12 and situated adjacent to the marker-signal crystal 15.

One electrode of the crystal 16 is connected to a common circuit connection 82. This circuit is also connected to one end of a number of resistors including three resistors 85, 86 and 87. Also, there is an integrated circuit element 90 which acts as the amplifier. It has a feedback network including a resistor 91 and a capacitor 92 that are connected in parallel between the output of amplifier 90 and one input connection thereto. That same input connection also has a filter network connected thereto which includes a capacitor 95 with one side thereof connected to the other end of the resistor 85 which was mentioned above. Also, that same side of the capacitor 95 is connected to one electrode of the crystal 16.

The output of amplifier 90 goes via a circuit connection 98 to one end of a resistor 99. The other end of resistor 99 is connected to the base of a transistor 100. The output of the transistor 100 is connected to a light emitting diode 103 that is connected in series with a resistor 104 which has the other end thereof connected to a positive voltage supply circuit 105. The common circuit connection 105 leads from one side of a push button switch 109 that has the other side thereof connected to one side of a power supply switch 110. The other side of switch 110 is connected to a positive potential circuit connection 112. It may be noted that the circuit connection 105 also goes to one end of another resistor 115 that has the other end thereof connected to the common circuit connection 82.

It will be appreciated that the circuit constants of the amplifier system according to FIG. 3 will be chosen so as to provide a desired response in decibels for the amplifier and filter together so that the maximum frequency response will correspond to the predetermined frequency of the marker signal generator which was described above and illustrated in FIG. 4.

FIG. 2 illustrates how the simplicity of the invention lends itself to a compact structure. Thus, the reference numbers which are applied to the elements illustrated in FIG. 2, correspond with the reference numbers for the corresponding elements in the circuit diagrams of FIGS. 3 and 4. Also, it will be appreciated that the circuit board 20 of FIG. 2 is mounted within the housing 11 which also contains the battery or batteries to supply the DC potential.

An example of the circuit constants employed in a combined marker and test unit according to the invention is as follows:

| Oscillator unit (FIG. 4) | |
| --- | --- |
| Ref. No. | Circuit Value |
| 24 | CMOS-IC (hex buffer) |
| 50 | 200 K Ω |
| 51 | 100 K Ω |
| 53 | 10–110 pf |
| 71 | 0–2KΩ |

| Amplifier unit (FIG. 3) | |
| --- | --- |
| Ref. No. | Circuit Value |
| 90 | #741 IC |
| 85 | 220 K Ω |
| 86 | 10 K Ω |
| 95 | 150 pf |
| 91 | 1 M Ω |
| 92 | 2.5 pf |
| 87 | 82 Ω |
| 115 | 82 Ω |
| 99 | 1 K Ω |
| 100 | 2 N 3568 (transistor) |
| 103 | LED 5082-4403 |
| 104 | 220 Ω |

While a particular embodiment of the invention has been described above in considerable detail, in accordance with the applicable statutes, this is not to be taken as in any way limiting the invention but merely as being descriptive thereof.

I claim:

1. A combined pipeline marker and self test unit, comprising in combination
    a pipeline
    a first piezoelectric crystal bonded to said pipeline for emitting an acoustic marker signal having a predetermined frequency,
    a low power oscillator for driving said first crystal comprising
    a CMOS integrated circuit having six inverting buffers, circuit means including a capacitor and two resistors connected to a pair of said buffers for producing said predetermined frequency oscillation, three of said buffers being connected in parallel to drive said first crystal, and one of the said buffers being connected between said oscillation pair and said three drive buffers to isolate said oscillation pair, a second piezoelectric crystal bonded to said pipeline adjacent to said first piezoelectric crystal for detecting the presence of said marker signal, a low power amplifier for amplifying signals generated by said second crystals, comprising an integrated circuit amplifier, a discrete transistor connected to the output of said integrated amplfier, and filter means for connecting said second crystal to said integrated amplifier for tuning it to said predetermined oscillation frequency, a light emitting diode connected to the output of said transistor for indicating presence of said marker signal, and push button switch means for manually energizing said low power amplifier to test said marker operation.

* * * * *